United States Patent [19]
Eckert et al.

[11] Patent Number: 5,888,745
[45] Date of Patent: Mar. 30, 1999

[54] INTERFERENCE ELIMINATION REAGENT FOR THE DETERMINATION OF AN ANALYTE USING A METAL COMPLEX CAPABLE OF LUMINESCENCE

[75] Inventors: Bernhard Eckert, Weilheim; Helmut Lenz, Tutzing; Norbert Franken, Starnberg; Hans-Peter Josel, Weilheim; Beatus Ofenloch-Hähnle, Polling, all of Germany

[73] Assignee: Boehringer Mannheim GmbH, Mannheim, Germany

[21] Appl. No.: 655,476

[22] Filed: May 30, 1996

[30] Foreign Application Priority Data

May 31, 1995 [DE] Germany .................. 195 19 973.1

[51] Int. Cl.⁶ .................................................... G01N 33/53
[52] U.S. Cl. .................. 435/7.1; 435/7.8; 435/7.92; 435/7.93; 435/7.94; 435/6; 435/975; 436/501; 436/518; 436/536; 436/537; 436/543; 436/546; 436/75; 436/172
[58] Field of Search ................ 435/7.1, 7.8, 7.92, 435/7.93, 7.94, 6, 975; 436/501, 518, 536, 537, 543, 546, 73, 172

[56] References Cited

U.S. PATENT DOCUMENTS 4,810,635 3/1989 Ledden et al. .............................. 435/7
5,221,605 6/1993 Bard et al. .................................. 435/4

FOREIGN PATENT DOCUMENTS 0309230 3/1989 European Pat. Off. .
WO93124246 6/1993 WIPO .

OTHER PUBLICATIONS

Hemmila "Application of Fluorescence in ImmunoAssays" Wiley–Interscience Publication, John Wiley and Sons, Inc. New York, USA pp. 16–19, 34–35, 154–159, 1991.

Harlowe and Lane "Antibodies A Laboratory Manual" Cold Spring Harbor Laboratory, USA., 1988.

*Primary Examiner*—Paula K. Hutzell
*Assistant Examiner*—Heather A. Bakalyar
*Attorney, Agent, or Firm*—Fulbright & Jaworski, LLP

[57] ABSTRACT

The present invention concerns a method for the determination of an analyte in a sample liquid using a metal complex capable of luminescence as an analyte-specific marker group for the production of a measuring signal in which an unspecific metal complex is additionally added as an interference elimination reagent which has a structure that is chemically related to the marker group.

33 Claims, 6 Drawing Sheets

Ac-K-Ru(bpy)₃-UEUEUKUEUEUK-Ru(bpy)₃-UEUEUEUEUK-Ru(bpy)₃-U-NH2

HRuK, Testo-19-hs-DADOO-Ru-Phen

Ru(bpy)2-bpyCO2H

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 13
        ( B ) TYPE: amino acids
        ( C ) STRANDEDNESS: unknown -continued (D) TOPOLOGY: unknown (i i) MOLECULE TYPE: protein (i x) FEATURE:
  (D) OTHER INFORMATION: Each Xaa is bAla. The amino terminal
      lysine may be esterified to form Ru (bipyridyl)3. The
      carboxyl terminal lysine may also be esterified to form Ru
      (b i p y r i d y l)3. The carboxyl terminal carboxyl group may be
      acetylated.

(x i) SEQUENCE DESCRIPTION: SEQ ID NO: 1:

Lys  Xaa  Glu  Xaa  Glu  Xaa  Glu  Xaa  Glu  Xaa  Glu  Xaa  Lys
                 5                           1 0

INTERFERENCE ELIMINATION REAGENT FOR THE DETERMINATION OF AN ANALYTE USING A METAL COMPLEX CAPABLE OF LUMINESCENCE

BACKGROUND OF INVENTION

The present invention concerns a method for the determination of an analyte in a sample liquid using a metal complex capable of luminescence as an analyte-specific marker group for the production of a measuring signal and a reagent kit for carrying out this method.

DESCRIPTION OF THE PRIOR ART

The use of metal complexes capable of luminescence for detecting analytes in sample liquids and in particular in body fluids such as human sera is known. EP-A-0 178 450 discloses for example ruthenium complexes that are coupled to an immunologically active material and the ruthenium complexes contain three identical or different bicyclic or polycyclic ligands containing at least two nitrogen-containing heterocycles. EP-A-0 580 979 discloses the use of osmium or ruthenium complexes as marker groups for electrochemiluminescence. Nitrogen-containing heterocycles such as bipyridines are mentioned as ligands for these complexes. WO 87/06706 discloses further metal complexes which are suitable as marker groups for electrochemiluminescence measurements.

Metal complexes suitable for electrochemiluminescence measurements are also disclosed in DE 44 30 998.8, DE 44 39 345.8, DE 44 39 346.6 and DE 44 39 347.4.

A disadvantage in using metal complexes capable of luminescence as marker groups in the determination of analytes is that considerable interference can occur in particular samples and in particular in serum samples. These interferences occur so frequently in various test formats, especially in competitive assays, that this can represent a considerable impairment to routine diagnostic applicability. These interferences lead to a signal quenching i.e. the measured signal is low and, depending on the test format, false positive or negative analytical results are obtained.

It is known from the state of the art that components can be present in sera which react with immunological reagents and result in an analyte-independent modulation of the measured signal by cross-linking or changing the unspecific binding. This can lead to false recovery in the analyte determination. Interferences of this type can usually be eliminated by the addition of an immunological component that preferably reacts with interfering serum components and thus leads to an inactivation. However, such interference elimination reagents have not proven to be successful for the removal of the aforementioned interferences.

U.S. Pat. No. 4,810,635 describes the elimination of interference in a homogeneous apoenzyme reactivation immunoassay containing a flavin adenine dinucleotide (FAD) marker group in which a structural analogue of FAD e.g. flavin monocleotide (FMN) or riboflavin is added as an interference elimination reagent. An interference elimination reagent for metal complex marker groups which is suitable for heterogeneous test formats in particular is neither disclosed nor implied.

SUMMARY OF THE INVENTION

The object of the present invention was therefore to provide an interference elimination reagent for test procedures for the determination of analytes using metal complexes capable of luminescence as marker groups which, on the one hand, enables a reliable elimination of interference by interfering components in sera and, on the other hand, does not significantly impair the accuracy and sensitivity of the test.

This object is achieved by a method for the determination of an analyte in a sample liquid using a metal complex capable of luminescence as an analyte-specific marker group for producing a measurable signal wherein an unspecific metal complex is additionally added as an interference elimination reagent which has a structure that is chemically related to the marker group.

In the method according to the invention for the determination of an analyte a metal complex capable of luminescence is used as an analyte-specific marker group to produce a measurable signal. This means that a metal complex capable of luminescence as defined in the following is directly or indirectly coupled to an analyte-specific test component and serves as a marker group for the specific detection of the analyte. In the case of a direct coupling the metal complex is covalently linked to an analyte-specific test component e.g. a receptor capable of binding to the analyte or to an analogue of the analyte. In the case of an indirect coupling the metal complex is for example covalently bound to a test component which itself is not analyte-specific but can react with an analyte-specific test component.

The metal complex used as the marker group can produce a detectable luminescence. The detection of this luminescence can for example be achieved by fluorescence or by electrochemiluminescence measurement. The detection is preferably achieved by electrochemiluminescence measurement.

The metal cation of the complex is a divalent or trivalent metal cation such as a transition metal or a rare earth metal. The metal is preferably ruthenium, osmium, rhenium, iridium, rhodium, platinum, palladium or chromium. Ruthenium, iridium, rhenium, chromium and osmium are especially preferred. Ruthenium is most preferred.

It was surprisingly found that the addition of an analyte-unspecific metal complex which has a structure that is chemically related to the marker group enables a partial or complete elimination of the interferences caused by signal quenching and on the other hand also does not lead to falsification of the measured results. The chemical structure of this unspecific complex is similar to that of the marker group used whereby this similarity can apply to the metal, the complex ligands and possibly to the linker structures used to couple the marker group to test components and to the carrier molecules.

The unspecific metal complex is preferably selected from transition metal and rare earth metal complexes and in particular from ruthenium, rhodium, osmium, nickel, iron, cobalt, iridium, palladium, platinum, chromium and rhenium complexes as well as combinations thereof. The unspecific metal complex is particularly preferably selected from rhodium, osmium, ruthenium and iron complexes as well as combinations thereof. Osmium and iron complexes are the most suitable since they have a particularly high structural similarity to the ruthenium complexes that are preferably used as marker groups. Iron complexes are preferred since they do not produce a significant signal in an electrochemiluminescence measurement under test conditions. Rhodium complexes are also preferred since they do not produce an electrochemiluminescence signal under test conditions. However, they have to be added in a somewhat larger amount in order to effectively eliminate interferences.

When using ruthenium complexes as marker groups, ruthenium interference eliminating complexes are also suitable e.g. if ruthenium is present bound to a peptide carrier. Osmium and ruthenium complexes which can produce an electrochemiluminescence signal under the test conditions are used especially in competitive assays as interference elimination reagents. Their use is less preferred in sandwich assays.

The ligands of the marker and interference elimination complexes should be as similar as possible in order to achieve an optimal interference elimination effect. Examples of suitable ligands are aromatic heterocyclic polydentate ligands e.g. nitrogen-containing heterocycles. Bipyridyl, bipyrazyl, terpyridyl and phenanthrolyl are preferred. The ligands are preferably selected from optionally substituted bipyridine and phenanthroline ring systems.

The unspecific interference elimination complex can be added as a complex alone, as a complex with a linker or/and as a carrier-bound complex. Since different interfering components sera can react differently to various interference elimination derivatives it may often be advantageous to use combinations of various interference elimination derivatives.

Examples of suitable carriers are substances which do not interfere with the determination of the analyte i.e. do not bind in an undesired manner with analyte-specific test components. In general any natural or synthetic substances can be used as carriers e.g. polymers or also small molecules provided that they are compatible with the other test components. Specific examples of suitable carriers are amino acids, peptides, proteins and polypeptides which can be optionally cross-linked, nucleotides, nucleic acids, synthetic carriers e.g. dextrans or nucleic acid analogues such as PNA (peptidic nucleic acids), carbohydrates or steroids. Examples of suitable polypeptides are albumins e.g. bovine serum albumin, unspecific immunoglobulins, immunoglobulin fragments, beta galactosidase and polylysine. Preferred carriers are nucleic acids, nucleic acid analogues, peptides or/and polypeptides. Carrier-bound complexes used which have a stoichiometry of complex to carrier of more than or equal to 1:1, i.e. which statistically contain at least one metal complex per carrier molecule preferred.

If the complex is used in a form coupled to a carrier or linker it may be preferable to use different complexes coupled to a single linker or carrier molecule or coupled to several similar linker or carrier molecules. On the other hand identical complexes can also be used coupled to different linkers or carriers or different complexes can be used coupled to different linkers or carriers. Even if the complexes are used alone, it is possible to use several different complexes e.g. complexes containing the same metal cations and different ligands, complexes containing different metal cations and the same ligands or complexes containing different metal cations and different ligands.

When carrying out the method according to the invention it is also preferable to use the unspecific metal complex in a stoichiometric excess relative to the analyte-specific marker group e.g. in an excess of up to $10^6:1$, in particular up to $10^5:1$.

The interference elimination complexes according to the invention can be produced by reacting a metal salt e.g. a metal halide with the appropriate ligands and optionally subsequently exchanging the halide ion for hexafluorophosphate, trifluoroacetate or tetrafluoroborate anions. Such processes are described in the state of the art e.g. in EP-A-0 178 450 and EP-A-0 255 534. Reference is hereby made to these disclosures.

The metal halides of the desired complexes are preferably reacted in a suitable solvent, e.g. water/ethanol or dimethylformamide, at room temperature or under reflux with two equivalents of a polyaza-bis-heterocycle e.g. 2,2'-bipyridine or phenanthroline. This complex is then reacted again with a further equivalent of the same or another ligand which can optionally contain a linker structure. A corresponding reaction scheme is shown in FIG. 1. The complexes without linkers obtained according to reaction path 1a can be used directly as an interference elimination reagent. The complexes with linkers obtained according to reaction path 1b can also be used directly as an interference elimination reagent or be coupled to a carrier.

Several methods of coupling to carriers are shown in FIG. 2. For this a reactive group e.g. an activated carboxylic acid group such as a carboxylic acid halogenide, carboxylic acid anhydride or an active ester e.g. an N-hydroxysuccinimide ester, a maleimide or a photoactivatable group e.g. an azide is firstly introduced into the complex. According to reaction paths 2a and 2b the activated complex can subsequently be reacted with carrier molecules e.g. proteins or peptide backbones. On the other hand metal complex-peptide conjugates can also be produced by a solid phase peptide synthesis from appropriate protected amino acid derivatives (e.g. FMOC derivatives) according to the processes described in DE-44 30 998.8 and DE-44 39 345.8. Reference is hereby made to this disclosure.

The metal complex is preferably detected in the method according to the invention by electrochemiluminescence in which luminescing species are produced electrochemically at the surface of an electrode. Examples for carrying out electrochemiluminescence assays with metal complexes of the state of the art are given in EP-A-0 580 979, WO 90/05301, WO 90/11511 and WO 92/14138. Reference is hereby made to the methods and devices for luminescence assays disclosed in these references. The electrochemiluminescence assays are preferably carried out as a heterogeneous assay in the presence of a solid phase which is particularly preferably composed of microparticles and especially of magnetic microparticles and which is provided with a reactive coating e.g. streptavidin. In this manner it is possible to detect immune complexes which contain a metal complex as a marker group in a bound form on the solid phase. On the other hand it is also possible to carry out the electrochemiluminescence measurement as a homogeneous assay (cf. e.g. EP-A-0 199 804; EP-A-0 265 519).

The electrochemiluminescence measurement is preferably carried out in the presence of a reducing agent for the metal complex e.g. an amine. Aliphatic amines are preferred and in particular primary, secondary and tertiary alkylamines whose alkyl groups each have 1 to 3 carbon atoms. Tripropylamine is particularly preferred. However, the amine can also be an aromatic amine such as aniline or a heterocyclic amine. The reducing agent can already be integrated into the ligand sphere of the complex.

In addition a non-ionic surface-active agent e.g. an ethoxylated phenol or an alcohol can optionally be present as an amplifier. Such substances are for example obtainable under the names Triton-X 100, Triton-N 401 and Thesit.

On the other hand the luminescent metal complex can also be detected by fluorescence in which the complex is excited by irradiation with light of a suitable wavelength and the resulting fluorescence radiation is measured. Examples for carrying out fluorescence assays may be found in EP-A-0 178 450 and EP-A-0 255 534. Reference is hereby made to this disclosure.

In a preferred embodiment of the method according to the invention the analyte is determined in an immunoassay. Examples of analytes which can be determined in an immunoassay are antigens or haptens. In this case the analyte is detected by reaction with one or several specific antibodies. On the other hand an immunoassay can also be carried out to determine immunoglobulins in a sample solution by reaction with specific antigens. In a further preferred embodiment the analyte is determined in a nucleic acid hybridization assay. This embodiment serves in particular to determine nucleic acid analytes.

In the method according to the invention the analyte can be determined in a sandwich assay e.g. in a heterogeneous sandwich assay in which (a) the sample liquid containing the analyte is incubated in the presence of a reactive solid phase with at least two analyte-specific receptors one of which is bound to the solid phase or is present in a form capable of binding to the solid phase and another carries the metal complex marker group, (b) the solid phase is optionally separated from the incubation liquid and (c) the presence or/and the amount of the analyte in the solid phase or/and in the liquid phase is detected by determining the label.

Examples of analyte-specific receptors are antigens, haptens, antibodies, nucleic acids or nucleic acid analogues which enter into a specific immunological or hybridization reaction with the analyte to be determined. An example of a reactive solid phase is a streptavidin-coated solid phase to which a biotinylated receptor can bind. The labelled receptor can be directly or indirectly labelled. The analyte-specific receptor in a bindable form can also be composed of several components which are not linked covalently to one another but by affinity interaction (antibody-antigen; streptavidin/avidin-biotin).

In a sandwich assay an unspecific metal complex which does not generate an electrochemiluminescent signal, e.g. a rhodium or an iron complex, is preferably used as an interference elimination reagent.

On the other hand the analyte can also be determined in a competitive assay in a "labelled analogue" or "labelled receptor" format e.g. in a heterogeneous competitive assay in which (a) the sample liquid containing the analyte is incubated in the presence of a reactive solid phase with (a1) an analyte-specific receptor which is present bound to the solid phase or in a form bound to the solid phase or capable of binding to the solid phase and with an analyte analogue which carries the metal complex marker group or with (a2) an analyte analogue which is bound to the solid phase or is present in a form capable of binding to the solid phase and with an analyte-specific receptor which carries the metal complex marker group (b) the solid phase is optionally separated from the incubation liquid and (c) the presence or/and the amount of the analyte in the solid phase or/and in the liquid phase is detected by determining the label.

A component is used as the analyte analogue which competes with the analyte to be determined for an analyte-specific receptor.

The present invention in addition concerns a reagent kit for carrying out the method according to the invention comprising a metal complex capable of luminescence coupled to an analyte-specific component as the marker group and in addition an unspecific metal complex as the interference elimination reagent which has a structure that is chemically related to the marker group. The unspecific metal complex can be present as a complex alone, as a complex with a linker or/and as a carrier-bound complex as elucidated above.

BRIEF DESCRIPTION OF THE DRAWINGS

The invention is further elucidated by the following examples and figures. They show.

DESCRIPTION OF THE PREFERRED EMBODIMENT

Example 1

Figure 1:
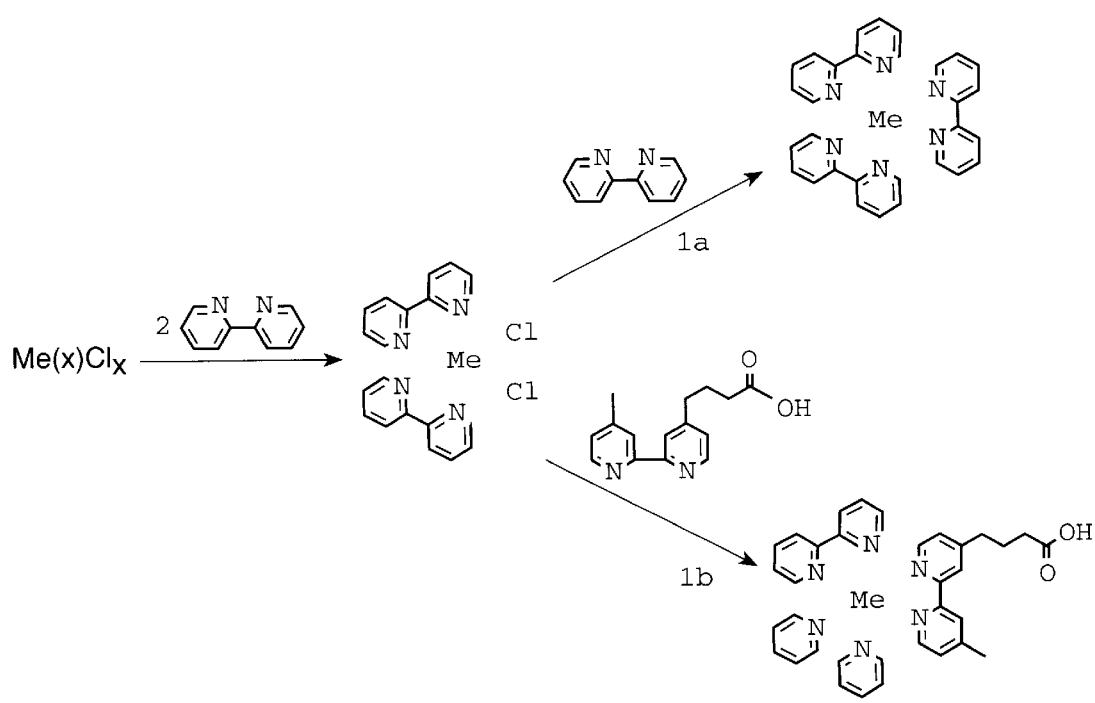
FIG. 1 a reaction scheme for producing metal complexes with or without a linker which are suitable as interference elimination reagents, FIG. 2 a reaction scheme for producing carrier-bound metal complexes that are suitable as interference elimination reagents, FIG. 3 a peptide ruthenium (bipyridyl)$_3$ conjugate, FIG. 4 a testosterone-Ru(bipyridyl)$_3$ conjugate, FIG. 5 a testosterone-Ru-bipyridyl conjugate with phenanthroline as complex ligands, FIG. 6 a Ru(bipyridyl)$_3$ complex with linker, FIG. 7 a Ru(bipyridyl)$_3$ complex with hydrophilic linker, FIG. 8 a Ru-bipyridyl complex with phenathroline as complex ligands and a hydrophilic linker and FIG. 9 a testosterone-peptide-Ru-(bipyridyl)$_3$-conjugate.
Figure 2:
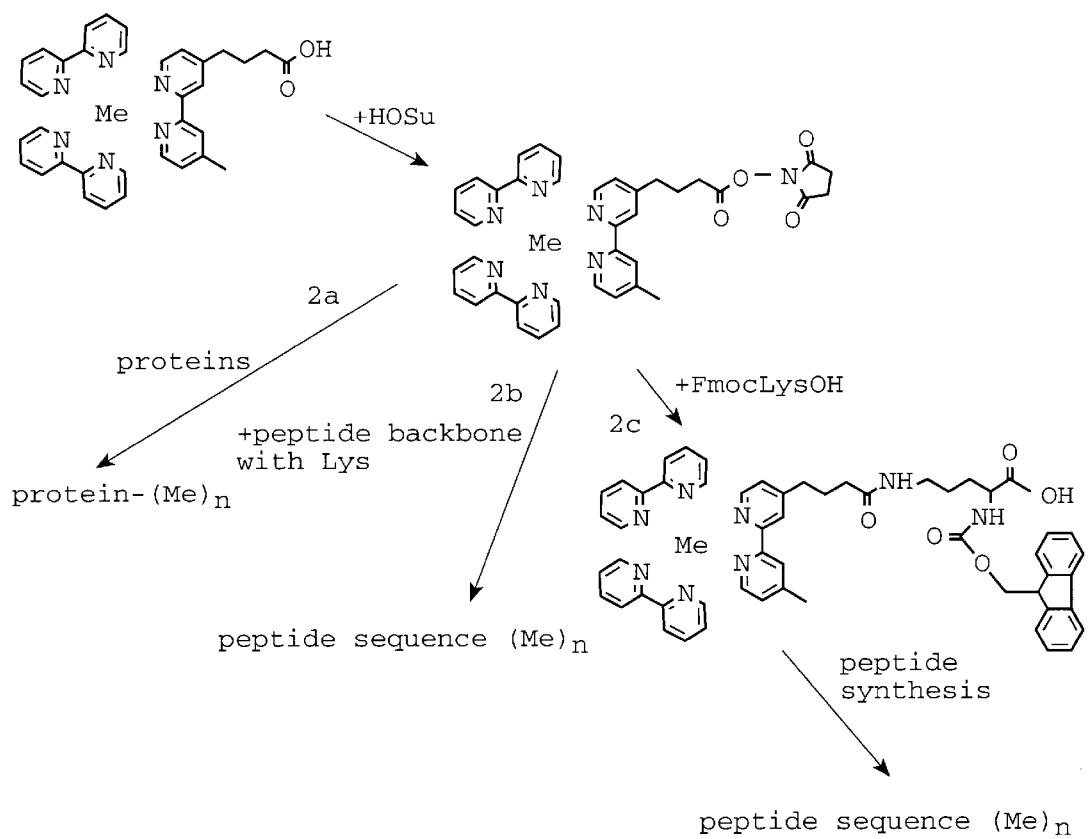

Production of interference elimination reagents 1.1 Fe(II)bpy$_3$(PF$_6$)$_2$

FeCl$_2$ (64 mg) and 2,2'-bipyridine (234 mg) are dissolved in 5 ml H$_2$O/ethanol (1:1) and stirred at room temperature. Then ethanol is removed by distillation, the aqueous solution is admixed with 2 equivalents NH$_4$PF$_6$. The resulting precipitate is suction filtered, rewashed and dried.
Yield: 250 mg red solid 1.2 Ni(II)bpy$_3$(PF$_6$)$_2$)

NiCl$_2$ (65 mg) is dissolved in 3 ml H$_2$O and admixed with a solution of 2,2'-bipyridine (240 mg) in 3 ml ethanol. The solvent is removed by distillation after 10 min, the residue is extracted with ethyl acetate, then dissolved in 10 ml H$_2$O and admixed with NH$_4$PF$_6$ (200 mg). The precipitate is suction filtered, rewashed and dried.
Yield: 380 mg pink solid
MS: M+: 671.1 (singly charged complex$^{++}$PF$_6$ $^-$cation)

1.3 Rh(III)bpy$_2$Cl$_3$

RhCl$_3$ (1.0 g) and 2,2-bipyridine (1.5 g) are admixed with 50 ml DMF and boiled for 3 hours. It is cooled to room temperature, the precipitated solid is filtered, rewashed and dried.
Yield: 1.41 g yellow solid
MS: M+: 485 (singly charged complex cation).

1.4 Rh(bpy$_3$(PF$_6$)$_3$

Rh(III)bpy$_3$Cl$_2$ (200 mg) and 2,2'-bipyridine (60 mg) are admixed with 20 ml H$_2$O and heated to boiling. 20 μl hydrazine hydrate solution is added and boiled for one hour. The solution is concentrated by evaporation and admixed with NH$_4$PF$_6$ (220 mg). The precipitate is suction filtered, rewashed and dried.
Yield: 310 mg yellow solid 1.5 Fe(II)bpy$_2$-4-[4(4'-methyl-2,2'bipyridyl)]-bpybutanoic acid-N-hydroxysuccinimide ester (PF$_6$)$_3$ a. Fe(II)bpy2-4-[4(4'-methyl-2,2'bipyridyl)]-butanoic acid (PF$_6$)$_3$ FeCl$_2$ (127 mg), 2,2'-bipyridine (312 mg) and 4-[4(4'-methyl-2,2'bipyridine]-butanoic acid (255 mg) are dissolved in 7 ml H$_2$O/ethanol (1:6) and stirred at room temperature. The solvents are then removed by distillation in a vacuum and the residue is purified by preparative HPLC (polygosil PR 18.5 μ, eluants: A:H$_2$O+0.1% TFA, B: acetonitrile+0.1% TFA, gradient: slowly from 10% B to 100% B). The clean fractions are lyophilized, the lyophilizate is dissolved in a small amount of water, admixed with aqueous NH$_4$PF$_6$ solution, the precipitate is suction filtered, rewashed and dried.

Yield: 140 mg red solid.

b. Fe(II)bpy$_2$-4 [4(4'-methyl-2,2'bipyridyl)]-bpybutanoic acid-N-hydroxysuccinimide ester (PF$_6$)$_3$ Fe(II)-bpy2-pbybutanoic acid (PF$_6$)$_2$ (53 mg) and N-hydroxysuccinimide (8.7 mg) are dissolved in 5 ml CH$_2$Cl$_2$, 2-(4-morpholinyl)-ethyl-isocyanide (8.3 μl) is added dropwise and the solution is stirred at room temperature. After complete reaction the solvent is removed by distillation in a vacuum, the residue is dissolved in acetone, the product is precipitated by addition of THF/diethyl ether, filtered and dried.

Yield: 52 mg red solid
MS: M+: 866.1 (singly charged complex$^{++}$-PF$_6$$^-$cation)
1H-NMR: O.K.

1.6 Rh(III)bpy$_2$-4-[4(4'-methyl-2,2'-bipyridyl)]-butanoic acid (PF$_6$)$_3$

Rh(bpy)$_2$Cl$_3$ (6.3 g) and 4-[4(4'-methyl-2,2'bipyridyl)]-butanoic acid (3.5 g) are heated to boiling in 400 ml of a water/ethanol mixture (9:1). A hydrazine-hydrate solution (0.73 ml, 80%) is added dropwise and then boiled for 3.5 hours under reflux. The solution is cooled, concentrated by evaporation to ca. 50 ml and purified over a SP Sephadex C-25 column. (Eluants: firstly HCl (c: 0.1 mol/l), then HCl (c: 0.1 mol/l)/NaCl (c: 0.5 mol/l)). The purified fractions are concentrated and admixed with an aqueous ammonium hexafluorophosphate solution. The precipitate is suction filtered, washed and dried.

Yield: 11.6 g white solid
MS: M+: 961.1 (singly charged complex$^{+++}$2(PF$_6$)$^-$cation)
$^1$H-NMR: O.K.

1.7 Rh(III)bpy$_2$-4-[4(4'-methyl-2,2'bipyridyl)]-bpybutanoic acid-N-hydroxysuccinimide ester (PF$_6$)$_3$ Rh(III)bpy$_2$-bpybutanoic acid (PF$_6$)$_3$ (10 g) and N-hydroxysuccinimide (1.05 g) are dissolved in 100 ml acetonitrile. Then 2-(4-morpholinyl)-ethyl isocyanide (1.4 ml) is added dropwise. After the reaction is completed the solution is concentrated, admixed with chloroform and stirred intensively. Afterwards the supernatant is decanted from the viscous solid, this is again dissolved in a small amount of acetonitrile and the process is repeated. Solvent residues are removed in a high vacuum.

Yield: 11 g beige solid
MS: M+: 1058.0 (singly charged complex$^{+++}$(PF$_6$)$_2$$^-$cation)
$^1$H-NMR: O.K.

1.8 Ru(II)bpyCO-ε-Lys-Fmoc

Fmoc-lysine-OH*HCl (3.8 g) and triethylamine (2.6 ml) in 70 ml DMF are added dropwise while stirring to Ru (bpy)$_2$-bpyCO-NHS ester (9.9 g) in 50 ml DMF (see EP-A-580 979). After one hour the DMF is removed by distillation in a high vacuum, the residue is dissolved in acetone, the solution is filtered, the filtrate is concentrated to ca. 50 ml and admixed with diethyl ether while stirring vigorously. After 14 hours the supernatant is decanted from the precipitated solid, this is again extracted with diethyl ether and solvent residues are removed.

Yield: 14 g red solid

The compound can be used directly in the peptide synthesis (cf. also DE-44 39 345.8, in which the synthesis of defined incorporated marker groups and haptens is described). Starting with an NHS ester it is also possible to directly synthesize hapten derivatives etc. On the other hand the compound can optionally be used directly as an interference elimination reagent after cleaving the Fmoc protecting group.

1.9 Metal complex-peptide conjugate

The peptide base (20 mg) is dissolved in DMF and admixed with 30 μl triethylamine. Equimolar amounts of the respective metal complex NHS ester are then added while stirring and it is stirred for a further one hour at room temperature. The solvent is afterwards removed by distillation in a vacuum and the residue is purified by means of preparative HPLC (Polygosil RP 18, 5μ, eluants: A: H$_2$O+ 0.1% TFA, B: acetonitrile+0.1% TFA, gradient: from 10% B slowly to 100% B).

The following metal complex peptide conjugate was prepared for example using the process described above (K=Lys, E=Glu, U=β-Ala):
peptide sequence: Ac-KUEUEUEUEUEUK-NH$_2$ (SEQ ID No. 1)
NHS-ester: Ru-(bpy)$_2$-bpyCO-NHS-ester
Yield: 60 mg Ac-K-Ru(bpy)$_3$-UEUEUEUEUEU-K-Ru(bpy) $_3$-NH$_2$ (residues 2–13 8 SEQ ID No. 1)
MS: M+:1344.5—doubly charged complex cation (2×RU$^+$ $_+$COO$^-$)
$^1$H-NMR: O.K.

Example 2

Production of metal complex conjugates with IgG and antibody fragments

Common commercial preparations of bovine IgG and sheep IgG can be used.

F(ab')$_2$ and Fab antibody fragments were prepared and purified from the corresponding IgG by cleaving with pepsin and papain according to Johnstone and Thrope (Immunochemistry in Practice p. 61f, Blackwell Scientific, 1987).

Polymerized bovine Fab fragments were produced by cross-linking bovine Fab with disuccinimidyl suberate according to EP-A-0 269 092.

The reaction of active esters of the metal complexes stated in example 1 with various IgG and antibody fragment preparations was carried out according to the process which is described in the following for three examples:

2.1 Ru(bpy)$_3$ conjugate with monoclonal anti-TSH-F(ab')$_2$ fragment stoichiometry 7.5:1

5 mg monoclonal anti-TSH-F(ab')$_2$ fragment is dissolved in 1 ml 0.15M K phosphate buffer, 0.15M NaCl, pH 7.8. Immediately before use 5 mg Ru(bpy)$_2$-bpy-CO-NHS ester (IGEN Inc., Rockville, USA) was dissolved in 0.75 ml anhydrous dimethyl sulfoxide. In order to achieve a molar ratio of 7.5:1 based on the molecular weights 1075 for Ru(bpy)$_2$-bpy-CO-NHS ester and 100,000 for F(ab')$_2$, 0.369 mg Ru(bpy)$_2$-bpy-CO-NHS ester (59.4 μl) is added by pipette to the F(ab')$_2$ solution. The reaction vessel is incubated for 60 min at 25° C. In order to stop the reaction, 10 μl of a 1M lysine solution is added by pipette. The preparation is dialyzed for 24 hours against 25 mM K phosphate buffer/0.1M NaCl, pH 7.0 and then lyophilized.

Yield: 4.4 mg anti-TSH-F(ab')$_2$-Ru(bpy)$_3$$^{2+}$

An absorbance measurement at 455 nm of (ε=13.7) results in a molar ratio of incorporated label of 5.8–6.8:1 [Ru:F (ab')$_2$].

2.2 Bovine IqG-Rh(bpy)$_3$ 1:10

50 mg bovine IgG is dissolved in 5 ml 0.15M K-phosphate buffer, 0.15M NaCl, pH 7.8. Immediately before use 8 mg Rh(bpy)$_2$-bpy-CO-NHS ester is dissolved in 0.5 ml anhydrous dimethyl sulfoxide. In order to achieve a molar ratio of 10:1 based on the molecular weights 1203 for Rh(bpy)$_2$-bpy-CO-NHS ester and 150 000 for IgG, 4 mg Rh(bpy)$_2$-bpy-CO-NHS ester (250 μl) is added by pipette to the IgG solution while stirring. The reaction vessel is incubated for 60 min. at 25° C. In order to stop the reaction 10 μl of a 1M lysine solution is added by pipette. The mixture is dialyzed for 24 hours against 25 mM K phosphate buffer/0.1M NaCl, pH 7.0 and then lyophilized.

Yield: 46 mg bovine-IgG-Rh(bpy)$_3^{3+}$.

2.3 Bovine-Fab-Rh(bpy)$_3$ polymer 1:3.5

50 mg Bovine Fab polymer is dissolved in 5 ml 0.15K phosphate buffer, 0.15M NaCl, pH 7.8. Immediately before use 8 mg Rh(bpy)$_2$-bpy-CO-NHS ester is dissolved in 0.5 ml anhydrous dimethyl sulfoxide. In order to achieve a molar ratio of 3.5:1 based on t he molecular weights 1203 for Rh(bpy)$_2$-bpy-CO-NHS ester and 50 000 for Fab (as an individual building block in the polymer), 4.2 mg Rh(bpy)$_2$-bpy-CO-NHS ester (263 μl) is added by pipette to the Fab polymer solution while stirring. The reaction vessel is incubated for 60 min. at 25° C. In order to stop the reaction 10 μl of a 1M lysine solution is added by pipette. The mixture is dialyzed for 24 hours against 25 mM K phosphate buffer/0.1N NaCl, pH 7.0 and then lyophilized.

Yield: 38 mg bovine-Fab-Rh(bpy)$_3$ polymer

Example 3

TBC test

Test system:

In the TBC test the thyroxine binding capacity of serum is determined.

In the first reaction step a serum sample is admixed with a reagent which contains T4. In addition to T4 the reagent contains a T4 polyhapten biotin (T4-Bio-Ph; 70 ng/ml) as a major component. The added T4 binds to the binding proteins of the sample in an amount dependent on the binding capacity of the sample.

A buffer containing a polyclonal anti-T4 antibody Ru-bipyridyl derivative (100 ng/ml) is added in a second reaction step. In addition microparticles coated with streptavidin are added. The excess T4 from the first reaction competes with the T4-Bio-Ph for the labelled antibody. The labelled antibody bound to the T4 polyhapten is bound via biotin to the streptavidin-coated microparticles.

The microparticles are separated from the liquid phase in a measuring cell. In this process the labelled antibodies bound to the microparticles in an analyte-dependent amount remain bound to the solid phase. The ECL signal which is proportional to the concentration of the Ru-bipyridyl complex is generated electrochemically in the measuring cell and the analyte concentration is determined via a calibration curve.

Examination of the interference reducing effect:

In concurrent experiments samples (known interfering samples and normal samples) without or with an interference elimination substance are measured. As a reference the samples were additionally measured in an independent method. The derivatives used and their concentrations are listed in table 1.

Figures 3, 4:
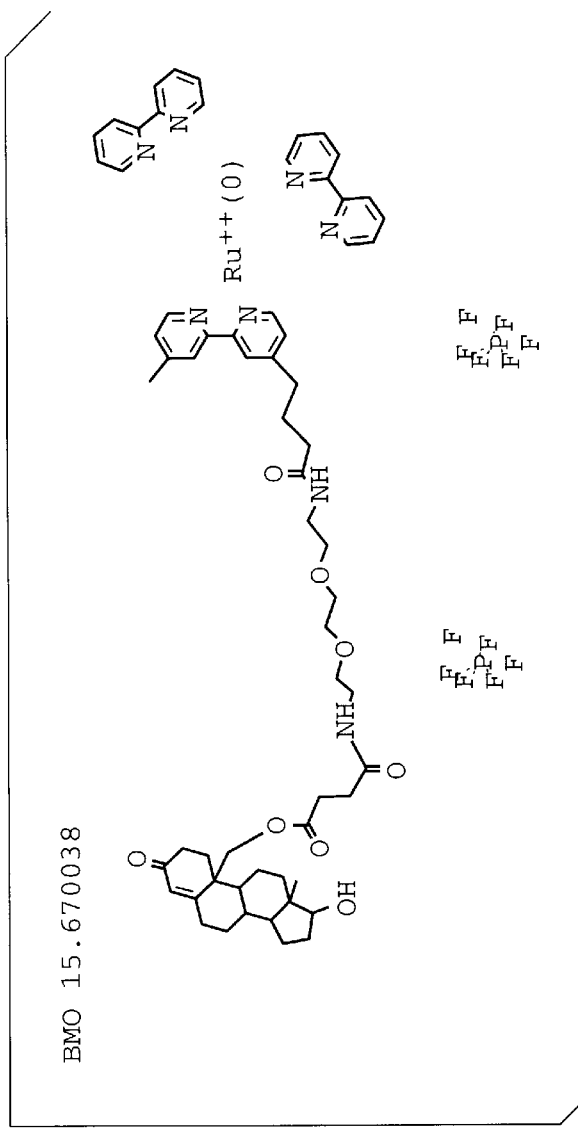
Figure 5:
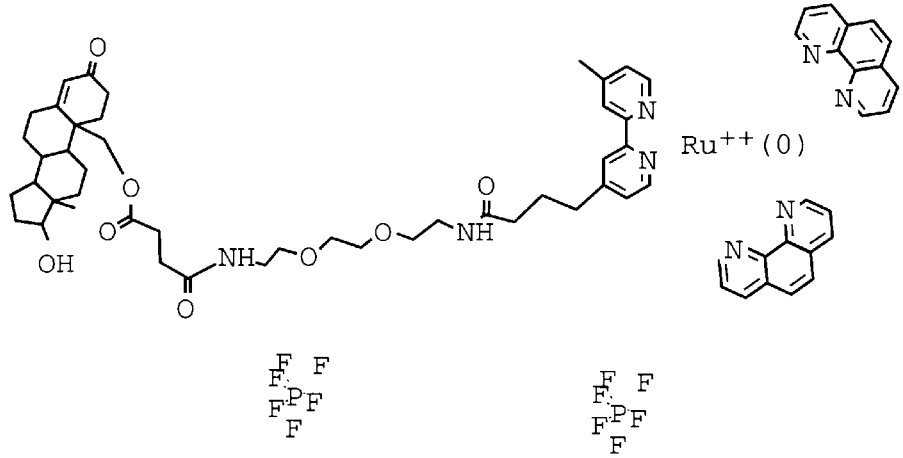
Figure 6:
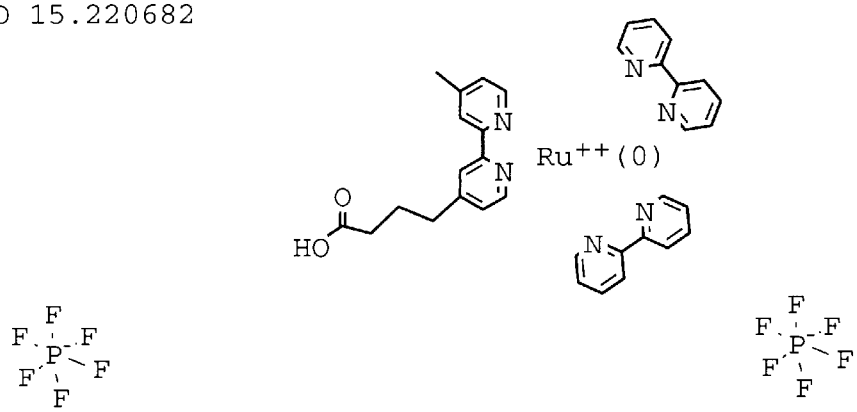
Figure 7:
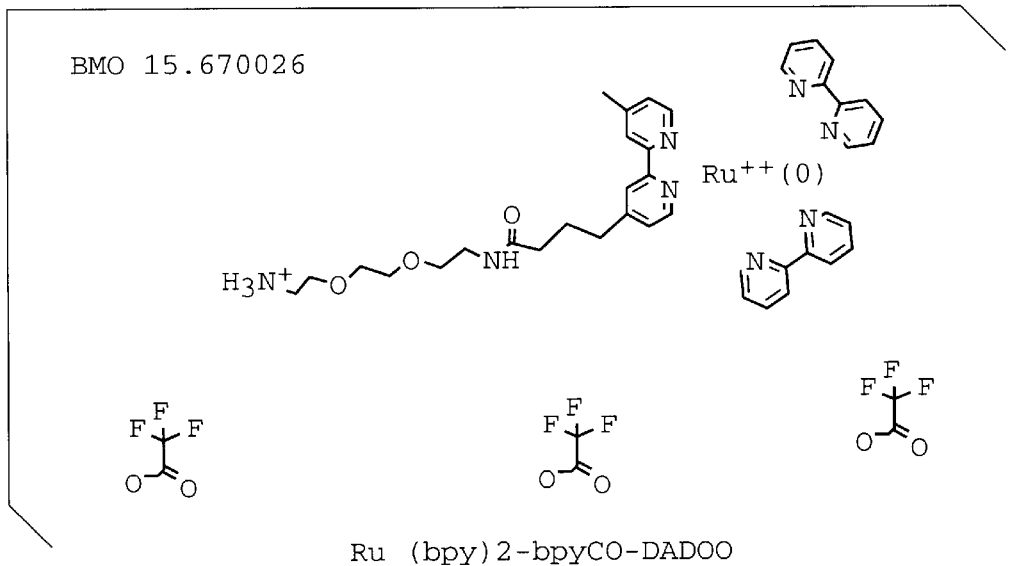
Figure 8:
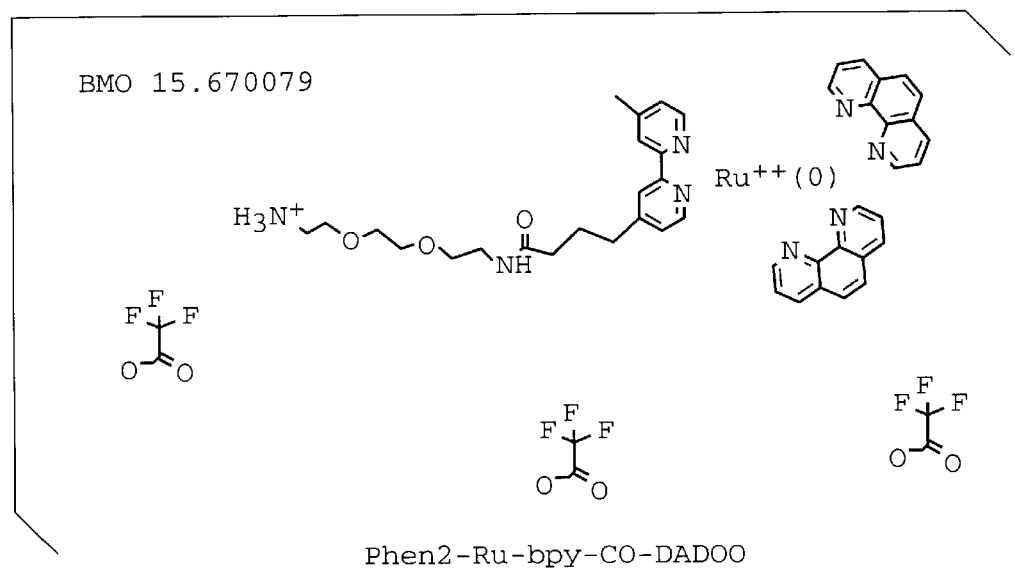
Figure 9:
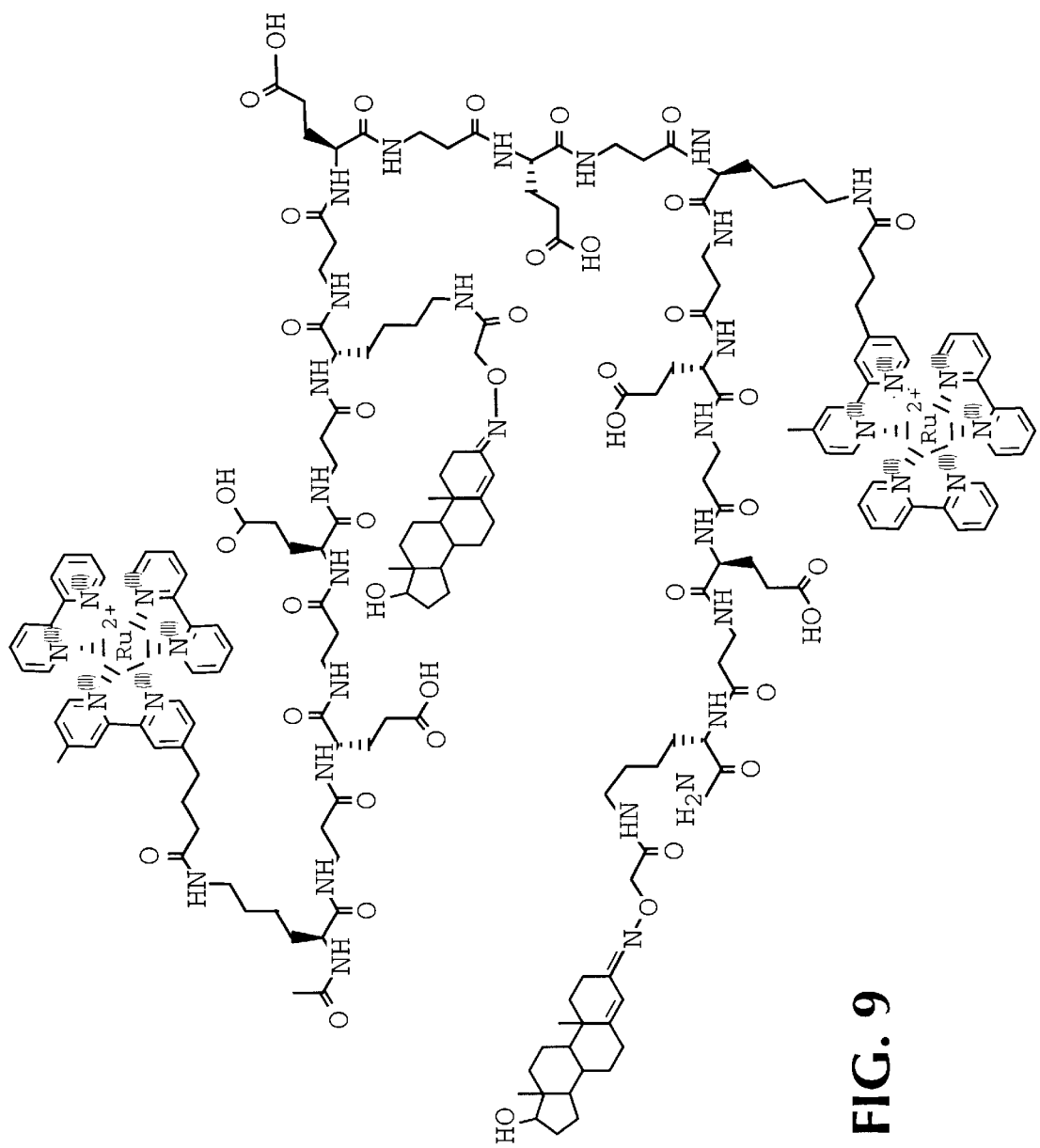

The following interference elimination reagents were used:

1: unspecific monoclonal antibody (IgG)-Os(bpy)$_3$ derivative (stoichiometry of carrier to label 1:12.5)
2: peptide-Ru(bpy)$_3$ conjugate (cf. FIG. 3)
3: unspecific polyclonal bovine antibody (Fab fragment)-Os(bpy)$_3$ derivative (stoichiometry 1:2.5)
4: cross-linked unspecific polyclonal bovine antibody (Fab fragment)-Os(bpy)$_3$ derivative (stoichiometry 1:2.5)
5. cross-linked unspecific polyclonal bovine antibody (Fab fragment)-Fe(bpy)$_3$ derivative (stoichiometry 1:2.5)
6: lysine-Ru(bpy)$_3$ (cf. example 1.8)
7: unspecific polyclonal bovine antibody (IgG)-Rh-(bpy)$_3$ derivative (stoichiometry 1:6)
8: unspecific polyclonal bovine antibody (IgG)-Rh(bpy)$_3$ derivative (stoichiometry 1:10)
9: cross-linked unspecific polyclonal bovine antibody (Fab fragment)-Rh(bpy)$_3$ derivative (stoichiometry 1:2)
10: cross-linked unspecific polyclonal bovine antibody (Fab fragment)-Rh(bpy)$_3$ derivative (stoichiometry 1:3.5)
11: unspecific polyclonal sheep antibody (IgG)-Rh(bpy)$_3$ derivative (stoichiometry 1:6)
12: unspecific polyclonal sheep antibody (IgG)-Rh(bpy)$_3$ derivative (stoichiometry 1:10)
13: testosterone-19-hs-diaminodioxaoctane-Ru(bpy)$_3$ conjugate (cf. FIG. 4)
14: peptide-Ru(bpy)$_3$ conjugate (cf. example 1.9)
15: testosterone-19-hs-DADOO-Ru-bipyridine-(phenanthroline)$_2$ conjugate (cf. FIG. 5)
16: Ru(bpy)$_2$-bpy-CO$_2$H (cf. FIG. 6)
17: Ru(bpy)$_2$-bpy-CO-DADOO (cf. FIG. 7)
18: Ru(phenanthroline)$_2$-bpy-CO-DADOO (cf. FIG. 8)
19: testosterone-peptide-Ru(bpy)$_3$ conjugate (cf. FIG. 9)

Result:

Depending on the type and concentration of the interference elimination component interfering sera have an improved recovery compared to reagents with no elimination of interference. The addition of interference elimination reagents does not cause a significant impairment of the test results in the case of normal sera.

TABLE 1

| interference elimination derivative | Conc. μg/ml | recovery in the TBC test (TBI) | | | | relative recovery (%) | | | |
|---|---|---|---|---|---|---|---|---|---|
| | | interfering sample 1 | interfering sample 2 | normal sample 1 | normal sample 2 | interfering sample 1 | interfering sample 2 | normal sample 1 | normal sample 2 |
| | | target value 1.13 | target value 0.9 | target value 1.15 | target value 1.05 | | | | |
| without | 0 | 0.38 | −1.27 | 1.121.12 | 1.02 | 34 | −141 | 97 | 97 |
| 1 | 1 | 0.87 | 0.66 | 1.25 | 1.16 | 77 | 73 | 109 | 110 |
| | 5 | 1.06 | 0.84 | 1.18 | 1.11 | 94 | 93 | 103 | 106 |
| | 10 | 1.1 | 0.91 | 1.19 | 1.12 | 97 | 101 | 103 | 107 |
| | 20 | 0.99 | 0.82 | 1.12 | 1.02 | 88 | 91 | 97 | 97 |

TABLE 1-continued

| derivative | Conc. µg/ml | recovery in the TBC test (TBI) | | | | relative recovery (%) | | | |
|---|---|---|---|---|---|---|---|---|---|
| | | interfering sample 1 | interfering sample 2 | normal sample 1 | normal sample 2 | interfering sample 1 | interfering sample 2 | normal sample 1 | normal sample 2 |
| 2 | 0.048 | 0.88 | 0.73 | 1.2 | 1.07 | 78 | 81 | 104 | 102 |
| | 0.096 | 1 | 0.86 | 1.18 | 1.11 | 88 | 96 | 103 | 106 |
| | 0.192 | 1.03 | 0.86 | 1.15 | 1.07 | 91 | 96 | 100 | 102 |
| | 0.348 | 1.06 | 0.86 | 1.15 | 1.07 | 94 | 96 | 100 | 102 |
| 3 | 1 | 0.52 | 0.08 | 1.12 | 0.99 | 46 | 9 | 97 | 94 |
| | 5 | 0.57 | 0.59 | 1.04 | 0.97 | 50 | 66 | 90 | 92 |
| | 10 | 0.66 | 0.6 | 1.03 | 0.94 | 58 | 67 | 90 | 90 |
| | 20 | 0.73 | 0.71 | 1.0B | 0.94 | 65 | 79 | 94 | 90 |
| 4 | 1 | 0.59 | 0.13 | 1.1 | 0.98 | 52 | 14 | 96 | 93 |
| | 5 | 1 | 0.58 | 1.06 | 1 | 88 | 64 | 92 | 95 |
| | 10 | 1.03 | 0.76 | 1.13 | 1.03 | 91 | 84 | 98 | 98 |
| | 20 | 1.03 | 0.73 | 1,03 | 1.04 | 91 | 81 | 90 | 99 |
| 5 | 5 | 0.77 | 0.3 | 1.13 | 1.07 | 68 | 33 | 98 | 102 |
| | 20 | 1.02 | 0.66 | 1.14 | 1.08 | 90 | 73 | 99 | 103 |
| | 100 | 1.13 | 0.85 | 1.1,5 | 1.08 | 100 | 94 | 100 | 103 |

| derivative | Conc. µg/ml | recovery in the TBC test (TBI) | | | | relative recovery (%) | | | |
|---|---|---|---|---|---|---|---|---|---|
| | | interfering sample 1 | interfering sample 2 | normal sample 1 | normal sample 2 | interfering sample 1 | interfering sample 2 | normal sample 1 | normal sample 2 |
| 6 | 0.0141 | 0.58 | −0.49 | 1.16 | 1.05 | 51 | −54 | 101 | 100 |
| | 0.028 | 0.56 | 0.29 | 1.17 | 1.06 | 50 | 32 | 102 | 101 |
| | 0.056 | 0.99 | 0.88 | 1.24 | 1.21 | 88 | 88 | 108 | 115 |
| | 0.112 | 1.35 | 1.4 | 1.21 | 1.64 | 119 | 119 | 105 | 156 |
| 7 | 57 | 0.72 | | 1.2 | 1.06 | 64 | | 104 | 101 |
| | 113 | 0.85 | | 1.18 | 1.08 | 75 | | 103 | 103 |
| | 227 | 0.96 | | 1.16 | 1.07 | 85 | | 101 | 102 |
| 8 | 57 | 0.92 | | 1.17 | 1.02 | 81 | | 102 | 97 |
| | 115 | 1.04 | | 1.17 | 0.09 | 92 | | 102 | 104 |
| | 230 | 1.08 | | 1.19 | 0.09 | 96 | | 103 | 104 |
| | 460 | 1.09 | 0.66 | 1.16 | 1.08 | 96 | 73 | 101 | 103 |
| | 500 | 1.15 | 0.77 | | 1.12 | 102 | 86 | | 107 |
| | 700 | 1.21 | 0.87 | | 1.13 | 107 | 97 | | 108 |
| | 1000 | 1.22 | 0.91 | | 1.15 | 108 | 101 | | 110 |
| 9 | 79 | 0.B2 | −0.17 | 1.21 | 1.12 | 73 | −19 | 105 | 107 |
| | 158 | 0.89 | 0.12 | 1.18 | 1.12 | 79 | 13 | 103 | 107 |
| | 317 | 0.94 | 0.22 | 1.14 | 1.07 | 83 | 24 | 99 | 92 |
| 10 | 86 | 1.03 | 0.28 | 1.11 | 1.06 | 91 | 31 | 97 | 101 |
| | 172 | 1.04 | 0.43 | 1.15 | 1.05 | 92 | 48 | 100 | 100 |
| | 344 | n.d. | n.d. | 1.15 | 1.08 | | | 100 | 103 |
| | 688 | 1.13 | 0.71 | 1.16 | 1.07 | 100 | 79 | 101 | 102 |

| derivative | Conc. µg/ml | recovery in the TBC test (TBI) | | | | relative recovery (%) | | | |
|---|---|---|---|---|---|---|---|---|---|
| | | interfering sample 1 | interfering sample 2 | normal sample 1 | normal sample 2 | interfering sample 1 | interfering sample 2 | normal sample 1 | normal sample 2 |
| 11 | 52 | 0.77 | 0 | 1.14 | 1.05 | 68 | 0 | 99 | 100 |
| | 104 | 0.85 | 0.31 | 1.16 | 1.1 | 75 | 34 | 101 | 105 |
| | 208 | 0.96 | 0.39 | 1.15 | 1.04 | 85 | 43 | 100 | 99 |
| 12 | 55 | 0.94 | 0.32 | 1.12 | 1.05 | 83 | 36 | 97 | 100 |
| | 111 | 1.02 | 0.51 | 1.12 | 1.08 | 90 | 57 | 97 | 103 |
| | 222 | 1.03 | 0.6 | 1.11 | 1.02 | 91 | 67 | 97 | 97 |
| | 440 | 1.06 | 0.7 | 1.13 | 1.05 | 94 | 78 | 98 | 100 |
| 13 | 0.0148 | 0.54 | −0.4 | 1.14 | 1.12 | 48 | −44 | 99 | 107 |
| | 0.03 | 0.55 | −0.16 | 1.17 | 1.09 | 49 | −18 | 102 | 104 |
| | 0.074 | 0.56 | 0.16 | 1.13 | 1.07 | 50 | 18 | 98 | 102 |
| 14 | 0.148 | 0.58 | 0.45 | 1.14 | 1.08 | 51 | 50 | 99 | 103 |
| | 0.035 | 0.46 | −0.66 | 1.2 | 1.07 | 41 | −73 | 104 | 102 |
| | 0.069 | 0.5 | −0.51 | 1.15 | 1.09 | 44 | −57 | 100 | 104 |
| | 0.174 | 0.51 | −0.42 | 1.16 | 1.08 | 45 | −47 | 101 | 103 |
| | 0.347 | 0.53 | −0.16 | 1.17 | 1.07 | 47 | −18 | 102 | 102 |
| | 13.88 | 0.75 | 0.77 | 1.08 | 0.98 | 66 | 86 | 94 | 93 |
| 15 | 0.009 | 0.45 | −0.75 | 1.21 | 1.04 | 40 | −83 | 105 | 99 |
| | 0.018 | 0.59 | −0.47 | 1.2 | 1.1 | 52 | −52 | 104 | 105 |
| | 0.045 | 0.58 | −0.19 | 1.18 | 1.09 | 51 | −21 | 103 | 104 |
| | 0.09 | 0.61 | 0.12 | 1.2 | 1.12 | 54 | 13 | 104 | 107 |
| 16 | 0.0475 | 0.43 | −0.41 | 1.16 | 1.06 | 38 | −46 | 101 | 101 |
| | 0.095 | 0.47 | −0.11 | 1.17 | 1.07 | 42 | −12 | 102 | 102 |
| | 0.19 | 0.54 | 0.19 | 1.18 | 1.09 | 48 | 21 | 103 | 104 |
| | 0.38 | 0.67 | 0.64 | 1.22 | 1.12 | 59 | 71 | 106 | 107 |
| | 0.74 | 0.74 | 0.78 | 1.2 | 1.2 | 65 | 87 | 104 | 106 |

| derivative | Conc. µg/ml | recovery in the TBC test (TBI) | | | | relative recovery (%) | | | |
|---|---|---|---|---|---|---|---|---|---|
| | | interfering sample 1 | interfering sample 2 | normal sample 1 | normal sample 2 | interfering sample 1 | interfering sample 2 | normal sample 1 | normal sample 2 |

TABLE 1-continued

| 17 | 1.118 | 0.61 | 0.08 | 1.18 | 1.08 | 54 | 9 | 103 | 103 |
|---|---|---|---|---|---|---|---|---|---|
|  | 0.594 | 0.68 | 0.76 | 1.12 | 1.07 | 60 | 84 | 97 | 102 |
|  | 1.188 | 1.02 | 1.19 | 1.29 | 1.27 | 90 | 132 | 112 | 121 |
| 18 | 0.118 | 0.71 | 0.79 | 1.2 | 1.19 | 63 | 88 | 102 | 113 |
|  | 0.594 | 0.58 | 0.1 | 1.11 | 1.03 | 51 | 11 | 97 | 98 |
|  | 1.188 | 0.36 | 1.19 | 1.54 | 2.21 | 32 | 132 | 134 | 210 |
| 19 | 0.04 |  | 0.47 |  | 1.01 |  | 52 |  | 96 |

Example 4

FT4 test

Test procedure:

In the FT4 test the free amount of thyroxine in the serum is determined.

In the first step a sample is incubated in an incubation vessel with a polyclonal anti-T4 antibody Fab fragment-Ru (bpy)$_3$ conjugate (50 ng/ml) in a phosphate buffer. In this process the free thyroxine present in the sample reacts with the antibody derivative.

In the second reaction step a component which contains biotin bound to T4 via a linker structure (2.5 ng/ml in phosphate buffer) is added. In addition microparticles coated with streptavidin are added.

The portion of antibody derivative which has not bound any free T4 from the sample can react with the T4 biotin derivative and be bound to the microparticles via a biotin-streptavidin interaction. After separating the microparticles, the ECL signal is generated on an electrode which is proportional to the bound amount of labelled antibody derivative. The signal generated and measured in this manner is read on a calibration curve and thus the analyte concentration is determined.

Results are shown in Table 2 in which a sample (known interfering samples and normal samples) with or without interference elimination reagent was measured. As a reference the samples were measured in an immunoassay which results in a correct clinical classification of the samples.

The interference elimination reagents 1, 2, 4, 5, 6, 8, 14, 16 and 19 described in example 2 were used. The following metal complex was also used as an interference elimination reagent:

20: Cross-linked unspecific polyclonal rabbit antibody (Fab fragment) Ru(bpy)$_3$ derivative (stoichiometry 1:2.5).

Result:

Addition of suitable interference elimination derivatives leads to a better recovery of the serum samples that were falsely recovered by the reagent with no interference elimination. When determining normal sera a significant interference is usually not found.

TABLE 2

|  |  | recovery in the FT4 (pmol/l) | | | | | relative recovery (%) | | | | |
|---|---|---|---|---|---|---|---|---|---|---|---|
| derivative | concentration | interfering serum 1 | interfering serum 2 | normal serum 1 | normal serum 2 | interfering serum 3 | interfering serum 1 | interfering serum 2 | normal serum 1 | normal serum 2 | interfering serum 3 |
|  |  | target value 13.0 | target value 19.7 | target value 14.6 | target value 18.7 | target value 18.0 |  |  |  |  |  |
| without | — | 24.4 | 52.6 | 14 | 16.1 | 22.9 | 187 | 268 | 96 | 97 | 127 |
| 2 | 75 nM | 15.4 | 20.6 | 14.6 | 18.8 | n.d. | 118 | 105 | 100 | 101 |  |
| 19 | 75 nM | 19.7 | 21.7 | 15.1 | 19.3 | n.d. | 151 | 110 | 104 | 103 |  |
| 1 | 10 μg/ml | 14.5 | 20.5 | 14.9 | 18.9 | n.d. | 111 | 104 | 102 | 101 |  |
| 4 | 10 μg/ml | 14.4 | 21 | 14.5 | 19.1 | n.d. | 111 | 107 | 100 | 102 |  |
| 5 | 20 μg/ml | 22.4 | 30.3 | 15.2 | 19.4 | n.d. | 172 | 154 | 104 | 104 |  |
| 20 | 5 μg/ml | 17.2 | 25.1 | 17.6 | 23.1 | n.d. | 132 | 128 | 121 | 124 |  |
| 6 | 800 ng/ml | 15.4 | 20.2 | 13.6 | 16.5 | n.d. | 118 | 103 | 93 | 88 |  |
| 8 | 1000 mg/ml | 13 | 21.3 | 14 | 17.2 | 18.7 | 100 | 108 | 96 | 92 | 104 |
| 16 | 3.84 μg/ml | 18.5 | 19.8 | 14.3 | 18.3 | 20.64 | 142 | 101 | 98 | 98 | 114 |
| 14 | 13.88 μg/ml | 20.8 | 21.8 | 15 | 19.6 | 22.8 | 160 | 111 | 103 | 105 | 126 |

We claim:

1. In a method for determining an analyte by adding to a liquid sample a substance which specifically binds said analyte and has attached thereto a first metal-containing complex capable of luminescence to provide a measurable signal, the improvement comprising: adding to the liquid sample, in an amount effective eliminate signal interference, a second metal-containing complex which does not specifically bind said analyte and is sufficiently structurally related to the first metal-containing complex to be capable of (a) luminescence and (b) reducing quenching of the first metal-containing complex's signal.

2. The method of claim 1, wherein the first metal-containing complex is a transition metal-containing complex or a rare earth metal-containing complex.

3. The method of claim 2, wherein said first metal-containing complex contains ruthenium, rhenium, iridium, chromium, or osmium.

4. The method of claim 3, wherein said first metal-containing complex contains ruthenium.

5. The method of claim 1, wherein said second metal-containing complex is a transition metal complex not specific for said analyte is a transition metal-containing complex or a rare earth metal-containing complex.

6. The method of claim 5, wherein said second metal-containing complex contains at least one member selected from the group complex consisting of ruthenium, rhodium, osmium, nickel, iron, cobalt, iridium, palladium, platinum, chromium, and rhenium.

7. The method of claim 6, wherein said at least one member is selected from the group consisting of rhodium, osmium, ruthenium, and iron.

8. The method of claim 1, wherein at least one of said first or second metal-containing complexes comprises a heterocyclic, polydentate ligand.

9. The method of claim 8, wherein said ligand is a bipyridyl, bipyrazyl, terpyridyl, or phenanthrolyl ligand.

10. The method of claim 1, wherein said second metal-containing complex is unattached to another substance.

11. The method of claim 1, wherein said second metal-containing complex is attached to a linker.

12. The method of claim 1, wherein said second metal-containing complex is bound to a carrier.

13. The method of claim 11, wherein said second metal-containing complex and attached linker are bound to a carrier.

14. The method of claim 12, wherein said carrier does not interfere with analyte determination.

15. The method of claim 13, wherein said carrier does not interfere with analyte determination.

16. The method of claim 14 or 15 wherein said carrier comprises a nucleotide, a nucleic acid molecule, a nucleic acid molecule analogue, an amino acid, a peptide, a polypeptide, a protein, a carbohydrate, or a steroid.

17. The method of claim 14 or 15 wherein said carrier and said second metal-containing complex are in a stoichiometric ratio of at least 1:1.

18. The method of claim 1, wherein said second metal-containing complex is added in stoichiometric excess relative to the first metal-containing complex.

19. The method of claim 1, comprising determining said analyte by determining electrochemiluminescence of said first metal-containing complex.

20. The method of claim 1, wherein said method is a heterogeneous assay.

21. The method of claim 1, wherein said method is a homogeneous assay.

22. The method of claim 1, wherein said method is an immunoassay.

23. The method of claim 1, wherein said method is a nucleic acid hybridization assay.

24. The method of claim 1, wherein said method is a sandwich assay.

25. The method of claim 24, wherein said method is a sandwich assay is a heterogeneous assay.

26. The method of claim 24, wherein said second metal-containing complex does not generate an electrochemiluminescent signal.

27. The method of claim 1, wherein said method is a competitive assay.

28. The method of claim 27, wherein said competitive assay is a heterogeneous assay.

29. A kit for determining an analyte in a liquid sample, comprising a separate portion of each of the following:
  (1) a substance which specifically binds said analyte and has attached thereto a first metal-containing complex capable of luminescence to provide a measurable signal, and;
  (2) a second metal-containing complex which does not specifically bind said analyte and is sufficiently structurally related to the first metal-containing complex to be capable of (a) luminescence and (b) reducing quenching of the first metal-containing complex's signal by a liquid sample.

30. The kit of claim 29, wherein said second metal-containing complex is unattached to a linker or a carrier.

31. The kit of claim 29, wherein the second metal-containing complex is attached to a linker.

32. The kit of claim 29, wherein said second metal-containing complex is attached to a carrier.

33. The kit of claim 31, wherein the second metal-containing complex and linker are attached to a carrier.

* * * * *

UNITED STATES PATENT AND TRADEMARK OFFICE
CERTIFICATE OF CORRECTION

PATENT NO. : 5,888,745
DATED : March 30, 1999
INVENTOR(S) : Bernhard Eckert, et al.

It is certified that error appears in the above-identified patent and that said Letters Patent is hereby corrected as shown below:

In cover page, in the section entitled Foreign Patent Documents, line 2, change "W093124246" to -- W09312424 --.
In cover page, in the section entitled Other Publications, line 2, change "Application" to -- Applications --.
In column 9, line 20, change "t he" to -- the --.
In column 11, line 9, Table, 5th column from left, change "1.0B" to -- 1.08 --.
In column 11, line 16, Table, 5th column from left, change "1,1,5" to -- 1.15 --.
In column 11, line 34, Table, 3rd column from left, change "0.B2" to -- 0.82 --.
In column 13-14, line 39, Table, 6th column from left, change "16.1" to -- 18.1 --.

Signed and Sealed this

Eighth Day of August, 2000

Attest:

Attesting Officer

Q. TODD DICKINSON

Director of Patents and Trademarks